US006452058B1

(12) United States Patent
Schweizer et al.

(10) Patent No.: US 6,452,058 B1
(45) Date of Patent: Sep. 17, 2002

(54) OXIDATIVE HALOGENATION OF $C_1$ HYDROCARBONS TO HALOGENATED $C_1$ HYDROCARBONS AND INTEGRATED PROCESSES RELATED THERETO

(75) Inventors: Albert E. Schweizer; Mark E. Jones; Daniel A. Hickman, all of Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 09/862,058

(22) Filed: May 21, 2001

(51) Int. Cl.$^7$ .................. C07C 17/15; C07C 27/00; C07C 51/14; C07C 2/00
(52) U.S. Cl. ................ 570/223; 570/243; 570/245; 570/254; 568/893; 562/520; 585/324; 585/642
(58) Field of Search .................. 570/223, 243, 570/245, 254; 568/893; 585/324, 642; 562/520

(56) References Cited

U.S. PATENT DOCUMENTS

| | | |
|---|---|---|
| 1,086,381 A | 2/1914 | Masland |
| 3,172,915 A | 3/1965 | Borkowski et al. ......... 260/614 |
| 3,657,367 A | 4/1972 | Blake et al. ............ 260/659 A |
| 3,894,107 A | 7/1975 | Butter et al. ............ 260/668 R |
| 4,471,150 A | 9/1984 | Wu ............................ 585/640 |
| 4,480,145 A | 10/1984 | Brennan et al. ............ 585/640 |
| 4,523,040 A | 6/1985 | Olah .......................... 568/671 |
| 4,737,594 A | 4/1988 | Olah .......................... 570/222 |
| 4,769,504 A | 9/1988 | Noceti et al. ............... 585/415 |
| 4,795,843 A | 1/1989 | Imai et al. .................. 585/408 |
| 4,990,696 A | 2/1991 | Stauffer ...................... 568/893 |
| 5,001,293 A | 3/1991 | Nubel et al. ................ 585/408 |
| 5,087,786 A | 2/1992 | Nubel et al. ................ 585/500 |
| 5,243,098 A | 9/1993 | Miller et al. ................ 568/893 |
| 5,354,916 A | 10/1994 | Horvath et al. ............. 568/893 |
| 5,397,560 A | 3/1995 | Millar et al. ................ 423/447 |
| 5,536,873 A | 7/1996 | Murphree et al. .......... 560/205 |
| 5,912,393 A | 6/1999 | Barger et al. ............... 585/640 |
| 5,969,195 A | 10/1999 | Stabel et al. ................ 568/700 |

FOREIGN PATENT DOCUMENTS

| | | |
|---|---|---|
| GB | 1373296 | 11/1974 |
| WO | WO 01/38271 | 5/2001 |
| WO | WO 01/38273 | 5/2001 |
| WO | WO 01/38275 | 5/2001 |
| WO | WO 01/42176 | 6/2001 |

OTHER PUBLICATIONS

"The Kinetics of the Hydrolysis of the Chlorinate Methanes," I. Fells, Fuel Society Journal, vol. 10, pp. 26–35, 1959.
"The Oxyhydrochlorination of Methane on Fumed Silica–Based Cu $^{+1}$, K, La Catalysts: I. Catalyst Synthesis," W. Pieters et al., Applied Cayalysis, vol. 11, pp. 35–48, 1984.
"The Oxyhydrochlorination of Methane on Fumed Silica–Based Cu, K, La Catalysts: II Gas Phase Stoichiometry," Wm. C. Connor, Jr., et al, Applied Catalysis, vol. 11, pp. 49–58, 1984.
"The Oxyhydrochlorination of Methane on Fumed Silica–Based Cu, K, La Catalysts: III Bulk & Surface Analysis," Wm. C. Connor, Jr. et al., Applied Catalysis, vol. 11, pp. 59–71, 1984.
"Selective Monohalogenation of Methane over Supported Acid or Platinum Metal catalysts and Hydrolysis of Methyl Halides over γ–Alumina–Supported Metal Oxide/Hydroxide Catalysts. A Feasible Path for the Oxidative Conversion of Methane into Methyl Alcohol/Dimethyl Ether," G. Olah et al, American Chemical Society, vol. 107, No. 24, pp. 7097–7105, 1985.
"Stabilization of the Active Phase by Interaction with the Support in $CuCl_2$ Oxychlorination Catalysts," E. Fortini et al, Journal of Catalysis, vol. 99, pp. 12–18, 1986.
"Effects of Pressure on the Oxyhydrochlorination of Methane," M. McDonald et al, Chemical Engineering Science, vol. 49, No. 24A, pp. 4627–4637, 1994.
K. Weissermel et al, "Industrial Organic Chemistry," $2^{nd}$ edition, VCH, Weinheim, pp. 168–175, 1993.
"Process For Vinyl Chloride Manufacture From Ethane And Ethlene With Secondary Refractive Consumption of Reactor Effluent HCI," filed in the United States on May 23, 2001, USSN 60/292,944 (Attorney's Docket No. 61831), Applicant: William D. Clark et al.
"Production of Vinyl Halide From Single Carbon Feedstocks," filed in the United States on May 23, 2001, USSN 60/292,945 (Attorney's Docket No. 61832), Applicant: William D. Clark et al.
"Oxidative Halogenation and Optional Dehydrogenation of C3+ Hydrocarbons," filed in the United States on May 23, 2001, USSN 60/293,123 (Attorney's Docket No. 61504A), Applicant: Albert E. Schweizer et al.

Primary Examiner—Alan Siegel

(57) ABSTRACT

An oxidative halogenation process involving contacting a reactant hydrocarbon selected from methane, a halogenated $C_1$ hydrocarbon, or a mixture thereof with a source of halogen and, preferably, a source of oxygen in the presence of a rare earth halide or rare earth oxyhalide catalyst, so as to form a halogenated $C_1$ hydrocarbon having a greater number of halogen substituents as compared with the reactant hydrocarbon. Preferably, the product is a monohalogenated methane, more preferably, methyl chloride. The oxidative halogenation process to form methyl halide can be integrated with downstream processes to produce valuable commodity chemicals, for example, methyl alcohol and/or dimethyl ether; light olefins, including ethylene, propylene, and butenes; higher hydrocarbons, including gasolines; vinyl halide monomer, and acetic acid. Hydrogen halide, which is a co-product of these downstream processes, can be recycled to the oxidative halogenation process.

58 Claims, No Drawings

OXIDATIVE HALOGENATION OF C₁ HYDROCARBONS TO HALOGENATED C₁ HYDROCARBONS AND INTEGRATED PROCESSES RELATED THERETO

BACKGROUND OF THE INVENTION

In a first aspect, this invention pertains to a process for the oxidative halogenation of methane or halogenated $C_1$ hydrocarbons. For the purposes of this discussion, the term "oxidative halogenation" shall refer to a process wherein methane or a halogenated $C_1$ hydrocarbon (the "reactant hydrocarbon") is contacted with a source of halogen and, optionally, a source of oxygen so as to form a halogenated $C_1$ hydrocarbon having a greater number of halogen substituents as compared with the reactant hydrocarbon. The oxidative chlorination of methane with hydrogen chloride in the presence of oxygen to form methyl chloride is an example of this process.

Monohalogenated methanes, such as methyl chloride, find utility in the production of silicones and higher halogenated methanes and can also be used as intermediates in the production of numerous commodity chemicals, for example, methanol, dimethyl ether, light olefins, including ethylene and propylene, and higher hydrocarbons, such as gasolines. Other halogenated $C_1$ hydrocarbons, such as dichloromethane, find utility as solvents, as intermediates for the manufacture of silicones, and in the methylation or etherification of cellulose, alcohols, and phenols, for example.

In a second aspect, this invention pertains to a process of preparing methyl alcohol and/or dimethyl ether by way of the oxidative halogenation of methane to form methyl halide and thereafter the hydrolysis of methyl halide to form methanol and/or dimethyl ether. Both methanol and dimethyl ether can be used as components in gasolines. Methanol, itself, can be used as a motor fuel, as a source of energy, and as a raw material feedstock for a variety of useful syntheses.

In a third aspect, this invention pertains to a process of preparing light olefins, such as ethylene, propylene, and butenes, and/or heavier hydrocarbons, such as C5+ gasolines, by way of the oxidative halogenation of methane to form methyl halide and the subsequent condensation of methyl halide to form light olefins and/or gasolines. Light olefins, such as ethylene, propylene, and butenes, are used as monomers in the production of poly(olefins), such as poly (ethylene), poly(propylene) and poly(butadienes), as well as being used as feedstocks for many valuable chemicals, for example, styrene, vinyl chloride monomer, cumene, and butadiene. The utility of gasolines is well known.

In a fourth aspect, this invention pertains to a process of preparing vinyl halide monomer using methane as a raw material. Vinyl halide monomer finds utility in the manufacture of poly(vinyl halide) polymers, notably poly(vinyl chloride).

In a fifth aspect, this invention pertains to a process of preparing acetic acid using methane as a raw material. Acetic acid finds wide utility in the manufacture of vinyl acetate and cellulose acetate, and in the production of important solvents, such as ethyl acetate, n-butyl acetate, isobutyl acetate, and methyl acetate.

As ready supplies and access to crude oil have become more uncertain, alternative sources of hydrocarbons and fuel have been sought out and explored. The conversion of natural gas, containing predominantly low molecular weight alkanes, to higher molecular weight hydrocarbons has received increasing consideration, as natural gas is generally available from readily secured and reliable sources. Large deposits of natural gas, chiefly composed of methane, are found in many locations throughout the world. In addition, low molecular weight alkanes are generally present in coal deposits and can be formed during mining operations, in various petroleum processes, and in the gasification or liquefaction of synthetic fuelstocks, such as, coal, tar sands, oil shale, and biomass. Moreover, in the search for petroleum, large amounts of natural gas are often discovered in remote parts of the world, such as remote parts of Western Canada, Australia, China, and the former Soviet Union, where there are no local markets for the use of natural gas as a fuel or as a chemical feedstock.

Much of the readily accessible natural gas is used in local markets as fuel in residential, commercial, and industrial applications. Typically, materials used as fuel are traded at prices below the prices commanded for chemical feedstocks. Use of natural gas as a chemical feedstock is, thus, a high-value application. Accessibility, however, is a major obstacle to the effective and extensive use of remote gas, whether for fuel or feedstock. In fact, vast quantities of natural gas are often flared, particularly in remote areas from which its transport in gaseous form is practically impossible.

Conversion of natural gas to useful chemical feedstocks, preferably liquid feedstocks, offers a promising solution to the problem of transporting low molecular weight hydrocarbons from remote locations; but conversions of this sort present a special challenge to the petrochemical and energy industries. The dominant technology now employed for utilizing remote natural gas involves its conversion to synthesis gas, also commonly referred to as "syngas," a mixture of hydrogen and carbon monoxide, with the syngas subsequently being converted to liquid products. Synthesis gas can be converted to syncrude, such as, with Fischer-Tropsch technology, and syncrude can then be upgraded to transportation fuels using typical refining methods. Alternatively, synthesis gas can be converted to liquid oxygenates, such as methanol, which in turn can be converted to more conventional transportation fuels via certain zeolitic catalysts.

While syngas processing provides a means for converting natural gas into a more easily transportable liquid that in turn can be converted into useful chemical products, the intermediate step involved in such processing, i.e., the formation of the synthesis gas, is disadvantageously costly. The cost occurs in adding oxygen to the substantially inert methane molecule to form the syngas mixture of hydrogen and carbon monoxide, and occurs again in removing the oxygen when hydrocarbons are the desired end-product. As a further disadvantage, if synthesis gas is to be used to make methanol or hydrocarbon products, the syngas should be made at high pressure and high temperature to achieve acceptable syngas formation rates. Accordingly, a search continues for alternate means of converting methane directly to more valuable chemical feedstocks.

A potential alternate route to activating methane involves its oxidative halogenation in a first step to form methyl halide or other lower halogenated methanes, e.g., dihalomethanes, which can then be converted in a second step into valuable commodity chemicals, such as methanol, dimethyl ether, light olefins, and higher hydrocarbons, including gasoline. When applied to chlorine halogenation, this route has been referred to as the "chlorine-assisted" route, which can be represented by the following two-step process (I) and (II):

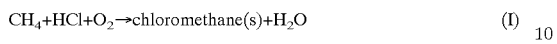   (I)

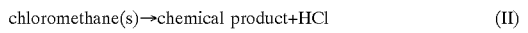   (II)

$CH_4 + HCl + O_2 \rightarrow$ chloromethane(s) $+ H_2O$   (I)

chloromethane(s) $\rightarrow$ chemical product $+ HCl$   (II)

For such a reaction scheme to be practical, the HCl generated in the second step should be efficiently recycled to the first step of the process.

Numerous references describe the catalyzed oxidative halogenation of methane to halogenated methanes, as noted for example in the following representative art: U.S. Pat. Nos. 3,172,915, 3,657,367, 4,769,504, and 4,795,843. Catalysts for the oxidative halogenation of hydrocarbons, such as methane, have typically consisted of first row transition metal halides, particularly, copper chloride, with promoters, such as potassium and lanthanum chlorides, supported on silica or alumina. Other common catalysts include iron compounds or cerium oxide, optionally, with one or more alkali or alkaline earth metal chlorides, and/or optionally, with one or more rare earth compounds, supported on an inert carrier, typically alumina, silica, or an aluminosilicate.

Disadvantageously, the oxidative halogenation processes cited hereinabove produce an unacceptable quantity of perhalogenated product, such as carbon tetrachloride, which is less desirable than less halogenated products, such as methyl chloride and dichloromethane. As a further disadvantage, the prior art processes produce an unacceptable quantity of deep oxidation products ($CO_x$), specifically, carbon monoxide and carbon dioxide. The production of lower value perhalogenated products and undesirable oxidized products irretrievably wastes the $C_1$ hydrocarbon feed and creates product separation and by-product disposal problems. As a further disadvantage, many of the transition metal halides, used as catalysts, exhibit significant vapor pressure at reaction temperatures; that is, these catalysts are volatile. The volatility generally produces a decline in catalyst activity and/or deposition of corrosive materials in downstream parts of the process equipment.

It is also known to monohalogenate methane with elemental halogen over supported acid or platinum metal catalysts to methyl halide and halogen acid, as disclosed, for example, in U.S. Pat. Nos. 4,523,040 and 5,354,916. The supported acid catalysts are disclosed to include ferric oxychloride, tantalum oxyfluoride, niobium oxyfluoride, zirconium oxyfluoride, and antimony oxyfluoride, supported on alumina. Disadvantageously, these prior art catalysts exhibit reaction rates and lifetimes that are too low for practical use. As a further disadvantage, the halogen acid formed must be converted back to elemental halogen and water, which makes the process uneconomical for most applications.

Pertaining to the second aspect of this invention, it is known to oxyhalogenate methane to methyl chloride and thereafter to hydrolyze methyl chloride to methyl alcohol and dimethyl ether, as illustrated, for example, by U.S. Pat. Nos. 1,086,381, 4,523,040, and 5,243,098. Conventional copper halide and platinum halide catalysts are disclosed for the oxyhalogenation step; zinc and magnesium oxides are disclosed for catalyzing the hydrolysis.

One skilled in the art knows that the current method of obtaining ethylene involves the steam cracking of ethane. Steam crackers are disadvantageously costly, complex, and energy intensive units that must be located at the site of oil refineries. More disadvantageously, steam-cracking produces complex mixtures of cracking products and hydrogen, which must undergo extensive and costly separations and purifications to obtain pure ethylene. In contrast, the synthesis of ethylene from methane via intermediate methyl halide should employ simpler engineering and less complex and less costly separations. In a related aspect, higher hydrocarbons, such as diesel oils and gasolines, can be manufactured via Fischer-Tropsch syntheses that require a syngas plant and complex separations operations of the Fischer-Tropsch product mixtures. Again, the route from methane to gasoline via intermediate methyl chloride should eliminate the need for a syngas plant and would greatly simplify separation efforts. Various patents disclose the condensation of methyl halides to light olefins and/or higher hydrocarbons, including, for example, U.S. Pat. Nos. 3,894,107, 5,087,786, and 5,397,560.

In addition to the above, U.S. Pat. No. 4,737,594 discloses a process for the manufacture of vinyl chloride by the condensation of methyl chloride, obtained from methane, followed by the oxychlorination of the condensation products and then by dehydrochlorination to vinyl chloride. The condensation step is taught to be carried out in the presence of a bifunctional catalyst, preferably, the oxides, oxyhalides, or sulfides of the transition metals of Groups IV, V, VI and VII of the Periodic Table. The oxychlorination is taught to be conducted in the presence of conventional copper chloride catalysts; while the dehydrochlorination is purely thermal.

The art also discloses preparing acetic acid via the oxidation of acetaldehyde, via alkane/alkene oxidations, via carbonylation of methanol, and via the conversion of synthesis gas, as discussed, for example, by K. Weissermel and H.-J. Arpe in *Industrial Organic Chemistry*, $2^{nd}$ ed., VCH Verlagsgesellschaft mbH, Germany, 1993, pp. 168–175. This art appears to be silent, however, with respect to preparing acetic acid starting from methane, but without the use of methanol intermediate.

Using halogen-assisted $C_1$ chemistry, based on methane as a raw material, for the preparation of the above-identified commodity chemicals will strongly depend upon halogenating methane with acceptable selectivity to methyl halide and, optionally, dichloromethane. Since the direct halogenation of methane with elemental halogen is substantially non-selective for methyl halide, and since the catalytic oxidative halogenation of methane is either non-selective for methyl halide or impractical, the current method of preparing methyl chloride, for example, depends on the reaction of methanol with hydrochloric acid. Accordingly, if $C_1$ chemistry based on the oxidative halogenation of methane to methyl halide and other lower halogenated methanes is to advance, then various improvements in prior art processes will be required. Specifically, an increase in selectivity to monohalogenated $C_1$ hydrocarbon is needed. Likewise, a reduction in selectivities to perhalogenated $C_1$ product and oxygenated products is needed. Also needed are an increase in catalyst activity and catalyst lifetime. With these improvements, the conversion of $C_1$ hydrocarbons, particularly methane, to halogenated $C_1$ hydrocarbons, particularly methyl halide, will be more attractive. Likewise, downstream applications, particularly, of monohalogenated methyl halides to methanol, dimethyl ether, vinyl halide monomer, acetic acid, light olefins, and higher hydrocarbons, including gasoline, will also be more attractive, thereby increasing the overall value of methane-based $C_1$ chemistry.

SUMMARY OF THE INVENTION

In one aspect, this invention provides for a novel oxidative halogenation process for preparing halogenated $C_1$ hydrocarbons. The novel process of this invention comprises contacting methane, a halogenated $C_1$ hydrocarbon, or a mixture thereof, the aforementioned compound(s) being referred to in various places hereinafter as the "reactant hydrocarbon," with a source of halogen and, optionally, a source of oxygen in the presence of a catalyst under process conditions sufficient to prepare a halogenated $C_1$ hydrocarbon product having a greater number of halogen substituents as compared with the reactant hydrocarbon. The catalyst used in the process of this invention comprises a rare earth halide or rare earth oxyhalide substantially free of copper and iron, with the proviso that when cerium is present in the catalyst, at least one other rare earth element is also present in the catalyst.

The novel oxidative halogenation process of this invention advantageously converts methane or a halogenated $C_1$ hydrocarbon, such as methyl chloride, in the presence of a source of halogen and, optionally, a source of oxygen into a halogenated $C_1$ hydrocarbon product having an increased number of halogen substituents as compared with the reactant hydrocarbon, i.e., methane or the reactant halogenated $C_1$ hydrocarbon, as the case may be. In this process, the use of a source of oxygen is preferred. In another preferred embodiment, the process of this invention can be beneficially employed to oxidatively chlorinate methane in the presence of hydrogen chloride and oxygen to form methyl chloride. Methyl chloride is beneficially employed in the preparation of methanol, dimethyl ether, light olefins, such as ethylene, propylene, and butenes, and higher hydrocarbons, including gasolines. As compared with prior art processes, the process of this invention advantageously produces the halogenated $C_1$ hydrocarbon in high selectivity with essentially no perhalogenated $C_1$ halocarbon, such as carbon tetrachloride, and low levels, if any, of undesirable oxygenates, such as, carbon monoxide and carbon dioxide. The lower selectivity to perhalogenated $C_1$ halocarbons and undesirable oxygenated by-products correlates with a more efficient use of reactant hydrocarbon, a higher productivity of the desired halogenated $C_1$ hydrocarbon product, and fewer separation and waste disposal problems.

In addition to the above advantages, the catalyst employed in the process of this invention does not require a conventional carrier or support, such as alumina or silica. Instead, the catalyst employed in this invention beneficially comprises a rare earth halide or rare earth oxyhalide that uniquely functions both as a catalyst support and as a source of a further catalytically active rare earth component. Unlike many heterogeneous catalysts of the prior art, the rare earth halide catalyst of this invention is beneficially soluble in water. Accordingly, should process equipment, such as filters, valves, circulating tubes, and small or intricate parts of reactors, become plugged with particles of the rare earth halide catalyst, then a simple water wash can advantageously dissolve the plugged particles and restore the equipment to working order. As a further advantage, the rare earth halide and rare earth oxyhalide catalyst employed in the process of this invention exhibit acceptable reaction rates and evidence of long lifetimes. Essentially no deactivation of these catalysts has been observed over the run times tested.

All of the aforementioned properties render the process of this invention uniquely attractive for converting methane and halogenated $C_1$ hydrocarbons into more highly halogenated $C_1$ hydrocarbons, which have utility in a variety of commercially significant syntheses. As a most preferred advantage, the process of this invention can monohalogenate methane selectively to methyl halides, including methyl chloride and methyl bromide, which are advantageously converted in downstream processes into valuable commodity chemicals, such as methyl alcohol, dimethyl ether, light olefins, gasolines, vinyl halide monomer, and acetic acid.

In a second aspect, this invention provides for a novel process of preparing methyl alcohol, dimethyl ether, or a combination thereof. The process in this aspect comprises (a) contacting methane with a source of halogen and, optionally, a source of oxygen in the presence of a catalyst comprising a rare earth halide or rare earth oxyhalide under monohalogenation process conditions sufficient to prepare methyl halide, the rare earth halide or rare earth oxyhalide catalyst being substantially free of copper and iron, with the proviso that when cerium is present in the catalyst, then at least one other rare earth element is also present in the catalyst; and thereafter (b) contacting the methyl halide thus produced with water under hydrolysis conditions sufficient to prepare methyl alcohol, dimethyl ether, or a combination thereof and co-product hydrogen halide; and optionally (c) recycling the co-product hydrogen halide to the oxidative halogenation process of step (a).

In this second aspect of the invention, methane is beneficially converted into methyl alcohol via intermediate methyl halide. The method of this invention advantageously produces methyl alcohol without the use of synthesis gas. Accordingly, a syngas reactor, which involves costly steam reforming or partial oxidation units, is not needed for the process of this invention. Instead, the engineering required for the process of this invention is conventional and cost effective. Accordingly, the process invention can be readily accommodated in remote locations around the world where methane sources are currently stranded. Since methyl alcohol is more easily and safely transported than methane gas, the conversion of methane to methyl alcohol by the simple process of this invention would free inaccessible methane resources.

In a third aspect, this invention provides for a novel process of preparing light olefins and/or gasolines. In this aspect, the process comprises (a) contacting methane with a source of halogen and, optionally, a source of oxygen in the presence of a catalyst comprising a rare earth halide or rare earth oxyhalide compound under oxidative halogenation process conditions sufficient to prepare methyl halide and, optionally, dihalomethane, the rare earth halide or rare earth oxyhalide catalyst being substantially free of copper and iron, and with the proviso that when cerium is present in the catalyst, at least one other rare earth element is also present in the catalyst; and thereafter (b) contacting the methyl halide and, optionally, dihalomethane thus produced with a condensation catalyst under condensation conditions sufficient to prepare at least one light olefin, a higher hydrocarbon, or a combination thereof, and co-product hydrogen halide; and optionally, (c) recycling the co-product hydrogen halide to the oxidative halogenation process of step (a). For the purposes of this third aspect of the invention, a "light olefin" shall be identified as ethylene, propylene, butenes, or a mixture thereof, and a "higher hydrocarbon" shall be identified as a C5+ hydrocarbon.

In this third aspect of the invention, methane is activated via intermediate methyl halide to form light olefins, such as ethylene, propylene, and/or butenes, and/or higher hydrocarbons, such as C5+ gasolines. In the production of light olefins, the novel process of this invention eliminates the need for costly, energy intensive, and complex steam cracker technology. Instead, highly valuable commodity olefins are produced with substantially simpler engineering while beneficially utilizing methane resources that are currently under-utilized or wasted. Likewise, the aforementioned novel process converts methane via intermediate methyl halide to C5+ gasolines. Thus, complicated hydrocarbon conversion processes that are associated with petroleum refineries and Fischer-Tropsch facilities are eliminated with the instant simpler invention.

In a fourth aspect, this invention provides for a novel process of preparing vinyl halide monomer. In this aspect, the process comprises (a) contacting methane with a first source of halogen and, optionally, a first source of oxygen in the presence of a first oxidative halogenation catalyst under oxidative halogenation process conditions sufficient to prepare methyl halide and, optionally, dihalomethane, the catalyst comprising a rare earth halide or rare earth oxyhalide, being substantially free of copper and iron, with the proviso that when cerium is present in the catalyst, then at least one other rare earth element is also present in the catalyst; (b) contacting the methyl halide and, optionally, dihalomethane thus produced with a condensation catalyst under condensation conditions sufficient to prepare ethylene and co-product hydrogen halide; (c) contacting the ethylene with a second source of halogen and, optionally, a second source of oxygen, in the presence of a second oxidative halogenation catalyst under oxidative halogenation process conditions sufficient to prepare vinyl halide monomer; and optionally (d) recycling the co-product hydrogen halide from step (b) to steps (a) and (c). Conversion of ethylene to vinyl halide monomer in step (c) can be effected by conventional prior art catalysts, for example, supported copper catalysts, that produce 1,2-dihaloethane, which subsequently is thermally cracked to vinyl halide monomer typically in a separate thermal cracker. Alternatively, conversion of ethylene to vinyl halide monomer in step (c) can be effected by use of the aforementioned catalyst comprising a rare earth halide or rare earth oxyhalide compound, essentially free of iron and copper, and with the proviso that when cerium is present in the catalyst, then at least one other rare earth element is also present in the catalyst. When the rare earth catalyst is used, then vinyl halide is formed directly without the need for a separate thermal cracking reactor. Vinyl halide can also be made by mixing the ethylene produced in step (b) with a methane feed to step (a) to yield a reactor effluent from step (a) containing methyl halide and vinyl halide. In this design, the first and second sources of halogen, the first and second sources of oxygen, and the first and second oxidative halogenation catalysts are in each instance identical, since steps (a) and (c) are combined in the same reactor. Accordingly, separation of methyl halide and vinyl halide prior to conversion of the methyl halide to ethylene provides a two-reactor system of producing vinyl halide from methane.

In this fourth aspect, the invention involves a novel integrated process for activating methane to form methyl halide, then condensing methyl halide to ethylene and co-product hydrogen halide, and thereafter, directly utilizing the stream containing ethylene and hydrogen halide in an oxidative halogenation process of converting ethylene to vinyl halide monomer. In a preferred method of conducting this process as described hereinabove, the step to produce methyl halide and the step to produce vinyl halide monomer are combined in one reactor. Accordingly, the process can be beneficially convert methane to vinyl halide monomer in a two-reactor system.

In a fifth aspect, this invention provides for a novel integrated process of preparing acetic acid. In this aspect the process comprises (a) contacting methane with a source of halogen and, optionally, a source of oxygen in the presence of an oxidative halogenation catalyst under oxidative halogenation process conditions sufficient to prepare methyl halide; (b) contacting the methyl halide thus produced with a carbonylation agent in the presence of a carbonylation catalyst under carbonylation conditions sufficient to prepared acetyl halide; and thereafter (c) hydrolyzing the acetyl halide under hydrolysis conditions to produce acetic acid. In a preferred embodiment of this invention, the oxidative halogenation catalyst comprises a rare earth halide or rare earth oxyhalide, being substantially free of copper and iron, with the proviso that when cerium is present in the catalyst, then at least one other rare earth element is also present in the catalyst In this fifth aspect of the invention, a novel synthesis is provided for the production of acetic acid. This unique synthesis is characterized by its use of methane as a raw material, the use of methyl halide as an intermediate in the production of acetic acid, and the absence of methanol as an intermediate in the process.

DETAILED DESCRIPTION OF THE INVENTION

In the novel oxidative halogenation process of this invention, a halogenated $C_1$ hydrocarbon product, preferably a monohalogenated $C_1$ hydrocarbon product, is selectively produced with essentially no formation of perhalogenated $C_1$ chlorocarbon product and with advantageously low levels of by-products, such as, $CO_x$ oxygenates (CO and $CO_2$). The novel process of this invention comprises contacting a reactant hydrocarbon selected from methane, a halogenated $C_1$ hydrocarbon, or a mixture thereof, with a source of halogen and, optionally, a source of oxygen in the presence of a catalyst under process conditions sufficient to prepare a halogenated $C_1$ hydrocarbon having a greater number of halogen substituents as compared with the reactant hydrocarbon. The use of a source of oxygen is preferred. The unique catalyst employed in the oxidative halogenation process of this invention comprises a rare earth halide or rare earth oxyhalide compound that is substantially free of copper and iron, with the further proviso that when cerium is present in the catalyst, at least one other rare earth element is also present in the catalyst.

In the process of this invention, the source of halogen may be provided, for example, as elemental halogen or hydrogen halide. If the source is elemental halogen, then the halogen itself functions in a dual role to provide a halogen ion and an oxidation agent for the oxidative halogenation process. In this instance, the reaction products will include a halogen acid. Advantageously, the halogen acid can be recycled and used with a source of oxygen in the feed to effect the process of this invention. Accordingly, there is no need to regenerate elemental halogen from the product halogen acid.

In a preferred embodiment, the process of this invention provides for the oxidative halogenation of methane to form methyl halide and, optionally dihalomethane. In this preferred embodiment, the process comprises contacting methane with a source of halogen and, optionally, a source of oxygen in the presence of the aforementioned rare earth halide or rare earth oxyhalide catalyst under process conditions sufficient to prepare methyl halide and, optionally, dihalomethane, the rare earth halide or rare earth oxyhalide catalyst being substantially free of copper and iron, and with the further proviso that when cerium is present in the catalyst, at least one other rare earth element is also present in the catalyst.

In a more preferred embodiment, the process of this invention provides for the oxidative monochlorination of methane to form methyl chloride in high selectivity. In this more preferred embodiment, the process comprises contacting methane with a source of chlorine, most preferably, hydrogen chloride, and a source of oxygen in the presence of a catalyst comprising lanthanum chloride or lanthanum oxychloride under process conditions sufficient to prepare methyl chloride, the lanthanum chloride or lanthanum oxychloride catalyst being substantially free of copper and iron.

In a more preferred embodiment of this invention, the rare earth halide or rare earth oxyhalide catalyst is "porous," which, for the purposes of this invention, means that the catalyst has a surface area of least about 3 $m^2/g$, as determined by the BET (Brunauer-Emmet-Teller) method of measuring surface area, described by S. Brunauer, P. H. Emmett, and E. Teller, *Journal of the American Chemical Society*, 60, 309 (1938), incorporated herein by reference. In another more preferred embodiment of this invention, the rare earth halide is lanthanum chloride, and the rare earth oxyhalide is lanthanum oxychloride.

The novel oxidative halogenation process, described hereinabove, may be beneficially integrated with downstream processes to convert methyl halides into highly valuable commodity chemicals, including methyl alcohol, dimethyl ether, light olefins, such as ethylene, propylene, and butenes, and higher hydrocarbons, including C5+ gasolines, as well as vinyl halide monomer and acetic acid.

Accordingly, in a second aspect, this invention provides for a novel process of preparing methyl alcohol, dimethyl ether, or a combination thereof. The process in this aspect comprises (a) contacting methane with a source of halogen and, optionally, a source of oxygen in the presence of a catalyst comprising a rare earth halide or rare earth oxyhalide under monohalogenation process conditions sufficient to prepare methyl halide, the rare earth halide or rare earth oxyhalide catalyst being substantially free of copper and iron, with the proviso that when cerium is present in the catalyst, then at least one other rare earth element is also present in the catalyst; and thereafter (b) contacting the methyl halide thus produced with water under hydrolysis conditions sufficient to prepare methyl alcohol, dimethyl ether, or a combination thereof and co-product hydrogen halide; and optionally (c) recycling the co-product hydrogen halide to the oxidative halogenation process of step (a).

In a third aspect, this invention provides for a novel process of preparing light olefins and/or gasolines, the process comprising (a) contacting methane with a source of halogen and, optionally, a source of oxygen in the presence of a catalyst comprising a rare earth halide or rare earth oxyhalide compound under oxidative halogenation process conditions sufficient to prepare methyl halide and, optionally, dihalomethane, the rare earth halide or rare earth oxyhalide catalyst being substantially free of copper and iron, and with the proviso that when cerium is present in the catalyst, at least one other rare earth element is also present in the catalyst; and thereafter (b) contacting the methyl halide and, optionally, dihalomethane thus produced with a condensation catalyst under condensation conditions sufficient to prepare at least one light olefin, a higher hydrocarbon, or a combination thereof, and co-product hydrogen halide; and optionally, (c) recycling the co-product hydrogen halide to the oxidative halogenation process of step (a). For the purposes of this third aspect of the invention, a "light olefin" shall be identified as ethylene, propylene, butenes, or a mixture thereof, and a "higher hydrocarbon" shall be identified as a C5+ hydrocarbon.

In a fourth aspect, this invention provides for a novel process of preparing vinyl halide monomer, the process comprising (a) contacting methane with a first source of halogen and, optionally, a first source of oxygen in the presence of a first oxidative halogenation catalyst under oxidative halogenation process conditions sufficient to prepare methyl halide and, optionally, dihalomethane, the catalyst comprising a rare earth halide or rare earth oxyhalide, being substantially free of copper and iron, with the proviso that when cerium is present in the catalyst, then at least one other rare earth element is also present in the catalyst; (b) contacting the methyl halide and, optionally, dihalomethane thus produced with a condensation catalyst under condensation conditions sufficient to prepare ethylene and co-product hydrogen halide; (c) contacting the ethylene with a second source of halogen and, optionally, a second source of oxygen, in the presence of a second oxidative halogenation catalyst under oxidative halogenation process conditions, and optional thermal cracking conditions, sufficient to prepare vinyl halide monomer; and optionally (d) recycling the co-product hydrogen halide from step (b) to steps (a) and (c).

Advantageously, the conversion of ethylene to vinyl halide monomer in step (c) hereinabove can be effected by conventional prior art catalysts, such as copper halides, or by use of the rare earth halide or rare earth oxyhalide compound, described previously. Vinyl halide can also be made by mixing the ethylene produced in step (b) with a methane feed to step (a) to yield a reactor effluent from step (a) containing methyl halide and vinyl halide.

In a fifth aspect, this invention provides for a novel integrated process of preparing acetic acid. In this aspect the process comprises (a) contacting methane with a source of halogen and, optionally, a source of oxygen in the presence of an oxidative halogenation catalyst under oxidative halogenation process conditions sufficient to prepare methyl halide; (b) contacting the methyl halide thus produced with a carbonylation agent in the presence of a carbonylation catalyst under carbonylation conditions sufficient to prepared acetyl halide; and thereafter (c) hydrolyzing the acetyl halide under hydrolysis conditions to produce acetic acid. In a preferred embodiment of this invention, the oxidative halogenation catalyst comprises a rare earth halide or rare earth oxyhalide, being substantially free of copper and iron, with the proviso that when cerium is present in the catalyst, then at least one other rare earth element is also present in the catalyst.

Each of above-identified downstream applications will be described in detail following a full description herein of the novel oxidative halogenation process.

The reactant hydrocarbon used in the oxidative halogenation process of this invention comprises methane or any halogenated $C_1$ hydrocarbon that is capable of acquiring halogen substituents in accordance with the process described herein. The halogen substituent of the halogenated $C_1$ hydrocarbon is preferably selected from chlorine, bromine, and iodine, more preferably, chlorine and bromine. One, two, or three halogen substituents may be present on the halogenated $C_1$ hydrocarbon; but for the purposes of the reactant hydrocarbon, the $C_1$ reactant is not a perhalogenated compound, as in carbon tetrachloride. Different halogen substituents may be suitably present in the $C_1$ hydrocarbon reactant, as illustrated by bromodichloromethane and dibromodichloromethane.

Suitable examples of halogenated $C_1$ hydrocarbons include, without limitation, methyl chloride, methyl bromide, methyl iodide, dichloromethane, dibromomethane, diiodomethane, chloroform, tribromomethane, bromodichloromethane, iododichloromethane, chlorodibromomethane, iododibromomethane, and the like. Methane is the most preferred reactant hydrocarbon. The $C_1$ reactant hydrocarbon may be provided to the oxidative halogenation process as a pure feed stream, or diluted with an inert diluent as described hereinafter, or as a mixture of methane and halogenated $C_1$ hydrocarbon, optionally, further in combination with an inert diluent.

The source of halogen, which is employed in the process of this invention, may be any inorganic or organic halogen-containing compound (or mixture of such compounds) that is capable of transferring its halogen atom(s) to the reactant hydrocarbon. Suitable non-limiting examples of the source of halogen include chlorine, bromine, iodine, hydrogen chloride, hydrogen bromide, hydrogen iodide, and halogenated hydrocarbons having one or more labile halogen substituents (i.e., transferable halogen substituents), the latter typically being perhalocarbons or highly halogenated hydrocarbons having three or more halogen atoms. Non-limiting examples of perhalocarbons with labile halogen substituents include carbon tetrachloride, carbon tetrabromide, and the like. Non-limiting examples of highly halogenated hydrocarbons having three or more halogen substituents, at least one substituent of which is labile, include chloroform and tribromomethane. Preferably, the source of halogen is a source of chlorine or a source of bromine, more preferably, hydrogen chloride or hydrogen bromide, most preferably, hydrogen chloride.

The source of halogen may be provided to the process in any amount that is effective in producing the desired halogenated $C_1$ hydrocarbon product. Typically, the amount of halogen source will vary depending upon the specific process stoichiometry, the reactor design, and safety considerations. It is possible, for example, to use a stoichiometric amount of halogen source with respect to the reactant hydrocarbon or with respect to oxygen, if oxygen is present. Alternatively, the source of halogen may be used in an amount that is greater or less than the stoichiometric amount, if desired. In one embodiment illustrative of the invention, methane can be oxidatively chlorinated with chlorine to form methyl chloride and hydrogen chloride, the stoichiometric reaction of which is shown hereinbelow in Equation III:

$$CH_4 + Cl_2 \rightarrow CH_3Cl + HCl \tag{III}$$

The aforementioned process, which does not employ oxygen, is typically conducted fuel-rich, that is, with an excess of hydrocarbon reactant; but the process conditions are not limited to fuel-rich modes of operation. Other operating conditions outside the fuel-rich limits may also be suitable. Typically, the molar ratio of reactant hydrocarbon to source of halogen (expressed as molecular halogen, for example, $Cl_2$) is greater than about 1/1, preferably, greater than about 2/1, and more preferably, greater than about 4/1. Generally, the molar ratio of reactant hydrocarbon to source of halogen is less than about 20/1, preferably, less than about 15/1, and more preferably, less than about 10/1.

In a preferred embodiment illustrative of the invention, methane can be oxidatively chlorinated with hydrogen chloride in the presence of oxygen to produce methyl chloride and water, the stoichiometric reaction of which is shown hereinafter in Equation IV:

$$CH_4 + HCl + \tfrac{1}{2}O_2 \rightarrow CH_3Cl + H_2O \tag{IV}$$

This type of reaction, which employs oxygen, is usually conducted "fuel-rich," due to safety considerations. The term "fuel-rich" means that oxygen is the limiting reagent and a molar excess of $C_1$ reactant hydrocarbon is used relative to oxygen. Typically, for example, the molar ratio of hydrocarbon to oxygen is chosen for operation outside the fuel-rich flammability limit of the mixture, although this is not absolutely required. In addition, a stoichiometric (e.g., 1 $HCl:0.5O_2$) or greater than stoichiometric molar ratio of hydrogen halide to oxygen is typically employed to maximize the yield of halogenated hydrocarbon product.

A source of oxygen is not required for the process of this invention; however, it is preferred to use a source of oxygen, particularly when the source of halogen contains hydrogen atoms. The source of oxygen can be any oxygen-containing gas or mixture of such gases, such as, essentially pure molecular oxygen, air, oxygen-enriched air, or a mixture of oxygen with a diluent gas that does not interfere with the oxidative halogenation process, such as, nitrogen, argon, helium, carbon monoxide, carbon dioxide, methane, and mixtures thereof. As noted above, when oxygen is employed, the feed to the oxidative halogenation reactor is generally fuel-rich. Typically, the molar ratio of reactant hydrocarbon to oxygen is greater than about 2/1, preferably, greater than about 4/1, and more preferably, greater than about 5/1. Typically, the molar ratio of reactant hydrocarbon to oxygen is less than about 20/1, preferably, less than about 15/1, and more preferably, less than about 10/1.

Based on the description hereinabove, one skilled in the art will know how to determine the molar quantities of reactant hydrocarbon, source of halogen, and source of oxygen suitable for reactant combinations different from those illustrated hereinabove.

Optionally, if desired, the feed, comprising reactant hydrocarbon, source of halogen, and preferred source of oxygen, can be diluted with a diluent or carrier gas, which may be any essentially non-reactive gas that does not substantially interfere with the oxidative halogenation process. The diluent may assist in removing products and heat from the reactor and in reducing the number of undesirable side-reactions. Non-limiting examples of suitable diluents include nitrogen, argon, helium, carbon monoxide, carbon dioxide, methane, and mixtures thereof. The quantity of diluent employed is typically greater than about 10 mole percent, and preferably, greater than about 20 mole percent, based on the total moles of feed to the reactor, i.e., total moles of reactant hydrocarbon, source of halogen, source of oxygen, and diluent. The quantity of diluent employed is typically less than about 90 mole percent, and preferably, less than about 70 mole percent, based on the total moles of feed to the reactor.

The catalyst employed in the oxidative halogenation process of this invention comprises, in one aspect, a rare earth halide compound. The rare earths are a group of 17 elements consisting of scandium (atomic number 21), yttrium (atomic number 39) and the lanthanides (atomic numbers 57–71) [James B. Hedrick, U.S. Geological Survey—Minerals Information—1997, "Rare-Earth Metals", incorporated herein by reference]. Preferably, herein, the term is taken to mean an element selected from lanthanum, cerium, neodymium, praseodymium, dysprosium, samarium, yttrium, gadolinium, erbium, ytterbium, holmium, terbium, europium, thulium, lutetium, and mixtures thereof. Preferred rare earth elements for use in the aforementioned oxidative halogenation process are those that are typically considered as being single valency metals. The catalytic performance of rare earth halides using multi-valency metals appears to be less desirable than those using single valency metals. The rare earth element for this invention is preferably selected from lanthanum, neodymium, praseodymium, dysprosium, yttrium, and mixtures thereof. Most preferably, the rare earth element used in the catalyst is lanthanum or a mixture of lanthanum with other rare earth elements.

Preferably, the rare earth halide is represented by the formula $MX_3$ wherein M is at least one rare earth element selected from the group consisting of lanthanum, cerium, neodymium, praseodymium, dysprosium, samarium, yttrium, gadolinium, erbium, ytterbium, holmium, terbium, europium, thulium, lutetium, and mixtures thereof; and wherein X is chloride, bromide, or iodide. More preferably, X is chloride, and the more preferred rare earth halide is represented by the formula $MCl_3$, wherein M is defined hereinbefore. Most preferably, X is chloride, and M is lanthanum or a mixture of lanthanum with other rare earth elements.

In a preferred embodiment, the rare earth halide is porous, meaning that typically the rare earth halide has a BET surface area of greater than about 3 $m^2/g$, preferably, greater than about 5 $m^2/g$. More preferably, the BET surface area is greater than about 10 $m^2/g$, even more preferably, greater than about 15 $m^2/g$, as an even higher preference, greater than about 20 $m^2/g$, and most preferably, greater than about 30 $m^2/g$. For these above measurements, a nitrogen adsorption isotherm was measured at 77K and the surface area was calculated from the isotherm data utilizing the BET method, as referenced earlier herein.

In another aspect, the catalyst employed in this invention comprises a rare earth oxyhalide, the rare earths being the seventeen elements identified hereinabove. Preferably, the rare earth oxyhalide is represented by the formula MOX, wherein M is at least one rare earth element selected from the group consisting of lanthanum, cerium, neodymium, praseodymium, dysprosium, samarium, yttrium, gadolinium, erbium, ytterbium, holmium, terbium, europium, thulium, lutetium, and mixtures thereof; and wherein X is selected from the group consisting of chloride, bromide, and iodide. More preferably, the rare earth halide is a rare earth oxychloride, represented by the formula MOCl, wherein M is defined hereinbefore. Most preferably, M is lanthanum or lanthanum with a mixture of other rare earth elements.

In a preferred embodiment, the rare earth oxyhalide is also porous, which generally implies a BET surface area of greater than about 12 $m^2/g$. Preferably, the rare earth oxyhalide has a BET surface area of greater than about 15 $m^2/g$, more preferably, greater than about 20 $m^2/g$, and most preferably, greater than about 30 $m^2/g$. Generally, the BET surface area of the rare earth oxyhalide is less than about 200 $m^2/g$. In addition, it is noted that the MOCl phases possess characteristic powder X-Ray Diffraction (XRD) patterns that are distinct from the $MCl_3$ phases.

In general, the presence in the catalyst of metals that are capable of oxidation-reduction (redox) is undesirable. Redox metals typically include transition metals that have more than one stable oxidation state, such as iron, copper, and manganese. The rare earth halide or oxyhalide catalyst of this invention is specifically required to be substantially free of copper and iron. The term "substantially free" means that the atom ratio of rare earth element to redox metal, preferably iron or copper, is greater than about 1/1, preferably greater than about 10/1, more preferably greater than about 15/1, and most preferably greater than about 50/1. In addition, cerium, a lanthanide rare earth element, is known to be an oxidation-reduction catalyst having the ability to access both the $3^+$ and $4^+$ oxidation states. For this reason, if the rare earth metal is cerium, the catalyst of this invention further comprises at least one more rare earth metal other than cerium. Preferably, if one of the rare earth metals is cerium, the cerium is provided in a molar ratio that is less than the total amount of other rare earth metals present in the catalyst. More preferably, however, substantially no cerium is present in the catalyst. By "substantially no cerium" it is meant that any cerium present is in an amount less than about 10 atom percent, preferably, less than about 5 atom percent, and even more preferably, less than about 1 atom percent of the total rare earth components.

In an alternative embodiment of this invention, the rare earth halide or rare earth oxyhalide catalyst, described hereinbefore, may be bound to, extruded with, or deposited onto a catalyst support, such as alumina, silica, silica-alumina, porous aluminosilicate (zeolite), silica-magnesia, bauxite, magnesia, silicon carbide, titanium oxide, zirconium oxide, zirconium silicate, or any combination thereof. In this embodiment, the conventional support is used in a quantity greater than about 1 weight percent, but less than about 90 weight percent, preferably, less than about 70 weight percent, more preferably, less than about 50 weight percent, based on the total weight of the catalyst and catalyst support.

It may also be advantageous to include other elements within the catalyst. For example, preferable elemental additives include alkali and alkaline earths, boron, phosphorous, sulfur, germanium, titanium, zirconium, hafnium, and combinations thereof. These elements can be present to alter the catalytic performance of the composition or to improve the mechanical properties (e.g. attrition-resistance) of the material. In a preferred embodiment, the elemental additive is calcium. In another preferred embodiment, the elemental additive is not aluminum or silicon. The total concentration of elemental additives in the catalyst is typically greater than about 0.01 weight percent and typically less than about 20 weight percent, based on the total weight of the catalyst.

The rare earth halide and rare earth oxyhalide compounds may be obtained commercially or prepared by methods published in the art. A method currently felt to be preferable for forming the porous rare earth oxyhalide (MOX) comprises the following steps: (a) preparing a solution of a halide salt of the rare earth element or elements in a solvent comprising either water, an alcohol, or mixtures thereof; (b) adding a base to cause the formation of a precipitate; and (c) collecting and calcining the precipitate in order to form the MOX. Preferably, the halide salt is a rare earth chloride salt, for example, any commercially available rare earth chloride. Typically, the base is a nitrogen-containing base selected from ammonium hydroxide, alkyl amines, aryl amines, arylalkyl amines, alkyl ammonium hydroxides, aryl ammonium hydroxides, arylalkyl ammonium hydroxides, and mixtures thereof. The nitrogen-containing base may also be provided as a mixture of a nitrogen-containing base with other bases that do not contain nitrogen. Preferably, the nitrogen-containing base is ammonium hydroxide or tetra (alkyl)ammonium hydroxide, more preferably, tetra($C_{1-20}$ alkyl)ammonium hydroxide. Porous rare earth oxychlorides may also be produced by appropriate use of alkali or alkaline earth hydroxides, particularly, with the buffering of a nitrogen-containing base, although caution should be exercised to avoid producing substantially the rare earth hydroxide or oxide. The solvent in Step (a) is preferably water. Generally, the precipitation is conducted at a temperature greater than about 0° C. Generally, the precipitation is conducted at a temperature less than about 200° C., preferably, less than about 100° C. The precipitation is conducted generally at about ambient atmospheric pressure, although higher pressures may be used, as necessary, to maintain liquid phase at the precipitation temperature employed. The calcination is typically conducted at a temperature greater than about 200° C., preferably, greater than about 300° C., and less than about 800° C., preferably, less than about 600° C. Production of mixed carboxylic acid and rare earth chloride salts also can yield rare earth oxychlorides upon appropriate decomposition.

A method currently felt to be preferable for forming the porous rare earth halide ($MX_3$) catalyst comprises the following steps: (a) preparing a solution of a halide salt of the rare earth element or elements in a solvent comprising either water, an alcohol, or mixtures thereof; (b) adding a base to cause the formation of a precipitate; (c) collecting, washing and calcining the precipitate; and (d) contacting the calcined precipitate with a halogen source. Preferably, the rare earth halide is a rare earth chloride salt, such as any commercially available rare earth chloride. The solvent and base may be any of those mentioned hereinbefore in connection with the formation of MOX. Preferably, the solvent is water, and the base is a nitrogen-containing base. The precipitation is generally conducted at a temperature greater than about 0° C. and less than about 200° C., preferably less than about 100° C., at about ambient atmospheric pressure or a higher pressure so as to maintain liquid phase. The calcination is typically conducted at a temperature greater than about 200° C., preferably, greater than about 300° C., but less than about 800° C., and preferably, less than about 600° C. Preferably, the halogen source is a hydrogen halide, such as hydrogen chloride, hydrogen bromide, or hydrogen iodide. More preferably, the halogen source is hydrogen chloride. The contacting with the halogen source is typically conducted at a temperature greater than about 100° C. and less than about 500° C. Typical pressures for the contacting with the source of halogen range from about ambient atmospheric pressure to pressures less than about 150 psia (1,034 kPa).

As noted hereinabove, the rare earth oxyhalide (MOX) compound can be converted into the rare earth halide ($MX_3$) compound by treating the oxyhalide with a source of halogen. Since the oxidative halogenation process of this invention requires a source of halogen, it is possible to contact the rare earth oxyhalide with a source of halogen, such as chlorine, in the oxidative halogenation reactor to form the $MX_3$ catalyst in situ.

The oxidative halogenation process of this invention can be conducted in a reactor of any conventional design suitable for gas phase processes, including batch, fixed bed, fluidized bed, transport bed, continuous and intermittent flow reactors, and catalytic distillation reactors. The process conditions (e.g., molar ratio of feed components, temperature, pressure, gas hourly space velocity), can be varied widely, provided that the desired halogenated $C_1$ hydrocarbon product, preferably monohalogenated $C_1$ hydrocarbon product, more preferably, methyl chloride, is obtained. Typically, the process temperature is greater than about 200° C., preferably, greater than about 300° C., and more preferably, greater than about 350° C. Typically, the process temperature is less than about 600° C., preferably, less than about 500° C., and more preferably, less than about 450° C. Ordinarily, the process can be conducted at atmospheric pressure; but operation at higher or lower pressures is possible, as desired. Preferably, the pressure is equal to or greater than about 14 psia (97 kPa), but less than about 150 psia (1,034 kPa). Typically, the total weight hourly space velocity (WHSV) of the feed (reactant hydrocarbon, source of halogen, optional source of oxygen, and optional diluent) will be greater than about 0.1 gram total feed per g catalyst per hour ($h^{-1}$), and preferably, greater than about 0.5 $h^{-1}$. Typically, the total gas hourly space velocity of the feed will be less than about 100 $h^{-1}$, and preferably, less than about 20 $h^{-1}$.

If the oxidative halogenation process is conducted as described hereinabove, then a halogenated $C_1$ hydrocarbon product is formed that has a greater number of halogen substituents as compared with the reactant hydrocarbon. Halogenated $C_1$ hydrocarbon products beneficially produced by the oxidative halogenation process of this invention include, without limitation, methyl chloride, dichloromethane, methyl bromide, dibromomethane, methyl iodide, chloroform, and tribromomethane. Preferably, the halogenated $C_1$ hydrocarbon product is a monohalogenated $C_1$ hydrocarbon, a dihalogenated $C_1$ hydrocarbon, or a combination thereof. More preferably, the halogenated $C_1$ hydrocarbon product is a monohalogenated $C_1$ hydrocarbon. Even more preferably, the halogenated $C_1$ hydrocarbon product is methyl chloride or methyl bromide; most preferably, methyl chloride.

For the purposes of the description herein, "conversion" shall be defined as the mole percentage of reagent compound that is converted in the oxidative halogenation process of this invention into product(s). Reference may be made to "conversion of reactant hydrocarbon," or "conversion of source of halogen," or "oxygen conversion." Conversions will vary depending upon the specific reactant being considered, specific catalyst, and specific process conditions. Typically, for the process of this invention, the conversion of methane or other reactant hydrocarbon is greater than about 3 mole percent, and preferably, greater than about 10 mole percent. Typically, for the process of this invention, the conversion of the source of halogen is greater than about 12 mole percent, and preferably, greater than about 20 mole percent. Typically, the oxygen conversion is greater than about 10 mole percent, and preferably, greater than about 20 mole percent.

For the purposes of this invention, "selectivity" shall be defined as the mole percentage of converted methane or other reactant hydrocarbon that is converted into a specific product, such as a halogenated $C_1$ hydrocarbon product or oxygenated by-product, such as CO or $CO_2$. In the oxidative halogenation process of this invention, the selectivity to monohalogenated $C_1$ hydrocarbon product, most preferably, methyl chloride or methyl bromide, is typically greater than about 60 mole percent, preferably, greater than about 70 mole percent, and more preferably, greater than about 80 mole percent. The selectivity to dihalogenated $C_1$ hydrocarbon product, preferably dichloromethane or dibromomethane, is typically less than about 20 mole percent, and preferably, less than about 15 mole percent. Advantageously, the oxidative halogenation process of this invention produces essentially no perhalogenated product, such as, carbon tetrachloride or carbon tetrabromide, which have lower commercial value. By "essentially no perhalogenated product", it is intended that not more than about five percent of perhalogenated species should be produced in the process and in combination with the desired halogenated $C_1$ hydrocarbon product, but preferably not more than about two percent, and most preferably not more than about one percent of perhalogenated species should be produced. As a further advantage, in preferred embodiments of this invention low levels of oxygenated by-products, such as $CO_x$ oxygenates (CO and $CO_2$) are produced. Typically, the total selectivity to carbon monoxide and carbon dioxide is less than about 20 mole percent, preferably, less than about 15 mole percent, and more preferably, less than about 10 mole percent.

The monohalogenated and dihalogenated hydrocarbon products, preferably, monohalogenated products, more preferably, methyl chloride or methyl bromide, that are produced in the oxidative halogenation process of this invention can be utilized as a feed in downstream processes that produce high-value commodity chemicals, such as methyl alcohol, dimethyl ether, light olefins, including ethylene, propylene, and butenes; higher hydrocarbons, including C5+ gasolines; vinyl halide monomer, and acetic acid. The hydrolysis of methyl halides to form methyl alcohol has been previously described in the art, representative citations of which include U.S. Pat Nos. 1,086,381, 4,990,696, 4,523,040, 5,969,195, and as disclosed by G. Olah in *Journal of the American Chemical Society,* 1985, 107, 7097–7105, and I. Fells, *Fuel Society Journal,* 10, 1959, 26–35, all of the aforementioned citations being incorporated herein by reference. For the example of methyl chloride hydrolysis to methyl alcohol, the process can be represented by the following stoichiometric reaction (V):

$$CH_3Cl+H_2O \rightarrow CH_3OH+HCl \qquad (V)$$

Any catalyst can be employed for the hydrolysis of methyl halides, provided that the hydrolysis produces methyl alcohol. Many catalysts exhibit activity for this hydrolysis including, for example, alumina; various zeolites of the ZSM structure code, such as ZSM-5, preferably, having a Constraint Index from 1 to 12; alkali and alkaline earth metal hydroxides and alkoxides, such as sodium hydroxide, potassium hydroxide, and sodium ethoxide; alkyl ammonium hydroxides and various amines, for example, trimethylamine hydroxide and piperidine; transition metal halide complexes, preferably, halide complexes of platinum, palladium, and nickel, and mixtures thereof, more preferably, the chloride complexes thereof, optionally including a cation of $H^+$, Group IA, or Group IIA elements, such as $K^+$ or $Na^+$; and metal oxide/hydroxide catalysts, including the metal oxides/hydroxides of Group IIA elements (e.g., Mg, Ba), the entire series of transition elements (e.g., V, Cr, Zr, Ti, Fe, or Zn), supported on γ-alumina or activated carbon.

The hydrolysis process conditions can vary depending upon the particular catalyst and alkyl halide employed. Since the thermodynamics favor the reverse reaction to form methyl halide (i.e., Equation V in reverse), an excess of water relative to methyl halide is typically employed to drive the equilibrium towards methyl alcohol. Preferably, the molar ratio of water to methyl halide is greater than about 1:1, more preferably, greater than about 5:1. Preferably, the water/methyl halide molar ratio is less than about 20:1, more preferably, less than about 10:1. Generally, the hydrolysis is conducted at a temperature greater than about 85° C., and preferably, greater than about 115° C. Generally, the hydrolysis is conducted at a temperature less than about 600° C., and preferably, less than about 400° C. The process pressure can also vary from subatmospheric to superatmospheric; but generally ranges from greater than about 7 psia (50 kPa), and preferably, greater than about 14 psia (97 kPa), to less than about 725 psia (4,999 kPa), and preferably, less than about 73 psia (500 kPa). The weight hourly space velocity (WHSV) of the methyl halide feed can vary widely from a value typically greater than about 0.1 g feed per g catalyst per hour ($h^{-1}$) to a value less than about 1,000 $h^{-1}$. Preferably, the weight hourly space velocity of the methyl halide feed ranges from greater than about 1 $h^{-1}$ to less than about 10 $h^{-1}$.

The conversion of methyl halide, that is, the molar percentage of methyl halide reacted relative to methyl halide in the feed, will vary depending upon the specific catalyst and process conditions. Generally, methyl alcohol and dimethyl ether are the predominant products, in varying ratios depending upon the catalyst and process conditions. Further details of the hydrolysis process and product distribution can be found in the pertinent references cited hereinabove. Hydrogen halide, which is a co-product of the hydrolysis process, can be conveniently recycled to the oxidative halogenation reactor, where it can be consumed as a source of halogen.

In another aspect of this invention, the methyl halide prepared by the aforementioned oxidative halogenation of methane can be condensed to form light olefins, such as ethylene, propylene, butenes, and higher hydrocarbons, including $C_{5+}$ gasolines. For the example of methyl chloride being converted into ethylene, the stoichiometric reaction can be represented by the following Equation (VI):

$$2CH_3Cl \rightarrow CH_2=CH_2+2HCl \qquad (VI)$$

As seen from the above, hydrogen halide, such as hydrogen chloride, is produced as a co-product of this condensation process. Again, the hydrogen halide can be conveniently recycled to the oxidative halogenation reactor and consumed as a source of halogen.

Any catalyst capable of effecting the condensation process can be employed. U.S. Pat. No. 5,397,560, for example, incorporated herein by reference, discloses the use of aluminosilicates having a DCM-2 structure code for the conversion of methyl halides into light olefins, predominantly ethylene and propylene. Catalysts known for the condensation of methyl alcohol to light olefins and gasolines can also be employed analogously for the condensation described herein of methyl halides into light olefins and gasolines. Non-limiting examples of such catalysts include zeolites of the ZSM structure code, such as ZSM-5, ZSM-11, ZSM-12, ZSM-34, ZSM-35, and ZSM-38, preferably, wherein the aforementioned ZSM zeolite has a Constraint Index from 1 to 12; as well as various aluminophosphates (ALPO's) and silicoaluminophosphates (SAPO's). References disclosing one or more of the aforementioned catalysts include U.S. Pat. Nos. 3,894,107, 4,480,145, 4,471,150, 4,769,504, 5,912,393, incorporated herein by reference.

Generally, the condensation process involves contacting methyl halide with the catalyst under condensation process conditions sufficient to prepare at least one light olefin, such as ethylene, propylene, butenes, or at least one $C_{5+}$ hydrocarbon, or any mixture thereof. The process temperature typically is greater than about 250° C., and preferably, greater than about 350° C. The process temperature is typically less than about 600° C., and preferably, less than about 450° C. The process pressure can vary from subatmospheric to superatmospheric; but generally a pressure greater than about 0.1 psi absolute (689 Pa) and less than about 300 psi absolute (2,068 kPa) is employed. The weight hourly space velocity (WHSV) of the methyl halide feed can vary widely from a value typically greater than about 0.1 g feed per g catalyst per hour ($h^{-1}$) to a value less than about 1,000 $h^{-1}$. Preferably, the weight hourly space velocity of the methyl halide feed ranges from greater than about 1 $h^{-1}$ to less than about 10 h$^{-1}$. The product distribution of the aforementioned condensation process will vary depending upon the specific feed, catalyst, and process conditions. A product stream comprising light olefins, predominantly ethylene, propylene, and butenes, is generally obtained with the DCM-2 catalyst. A product stream containing predominantly heavier hydrocarbons, such as $C_{5+}$ gasolines, is generally obtained with zeolite ZSM catalysts. Again, the hydrogen halide, obtained as a co-product of the process, can be conveniently recycled to the oxidative halogenation reactor and consumed as a source of halogen.

In a further application of this invention, ethylene obtained from the condensation of methyl halide can be fed directly into a vinyl halide monomer process, wherein the ethylene is contacted with a source of halogen, preferably the hydrogen halide, and optionally, a source of oxygen in the presence of an oxidative halogenation catalyst. Preferably, a source of oxygen is used. For the purposes of making vinyl halide monomer, the source of halogen and the source of oxygen can be any of those sources of halogen and sources of oxygen described hereinbefore in connection with the oxidative halogenation of methane. For the purposes of preparing vinyl halide monomer, the oxidative halogenation catalyst can be any conventional catalyst known for such a purpose, including supported copper catalysts, such as, supported copper chloride promoted with alkali or alkaline earth halides, known to those skilled in the art. When these conventional catalysts are used, then dihaloethane is obtained, which is subsequently thermally cracked to vinyl halide monomer. In a preferred embodiment, the oxidative halogenation catalyst is the rare earth halide or rare earth oxyhalide catalyst described hereinbefore in connection with the oxidative halogenation of methane. When the rare earth halide is used, then vinyl halide is obtained directly without the need for a separate thermal cracking reactor. Vinyl halide can also be made by mixing ethylene with the methane feed to the methane oxidative halogenation reactor so as to obtain an effluent containing both methyl halide and vinyl halide. Separation of methyl halide and vinyl halide prior to conversion of the methyl halide to ethylene beneficially provides a two-reactor system of producing vinyl halide from methane.

Typically, the molar ratio of ethylene to oxygen is greater than about 2/1, preferably, greater than about 4/1, and generally, less than about 20/1, and preferably, less than about 15/1. Generally, the oxidative halogenation of ethylene is carried out at a temperature greater than about 150° C., preferably, greater than about 200° C., and more preferably, greater than about 250° C. Typically, the oxidative halogenation of ethylene is carried out at a temperature less than about 500° C., preferably, less than about 425° C., and more preferably, less than about 350° C. Ordinarily, the process will be conducted at atmospheric pressure or a higher pressure. Typically, then, the pressure will be equal to or greater than about 14 psia (101 kPa), but less than about 150 psia (1,034 kPa). Typically, the total gas hourly space velocity (GHSV) of the reactant feed (ethylene, source of halogen, source of oxygen, and any optional diluent) will vary from greater than about 10 ml total feed per ml catalyst per hour (h$^{-1}$), preferably, greater than about 100 h$^{-1}$, to less than about 50,000 h$^{-1}$, and preferably, less than about 10,000 h$^{-1}$. Further details on a catalyst and process conditions suitable for the oxidative halogenation of ethylene-containing streams to vinyl halide monomer can be found in International Patent Application Serial No. PCT/US00/27272, filed Oct. 3, 2000, incorporated herein by reference.

In yet another aspect of this invention, the methyl halide, produced in the oxidative halogenation of methane, can be carbonylated with a carbonylation agent in the presence of a carbonylation catalyst to form acetyl halide, which thereafter can be hydrolyzed to form acetic acid. In the carbonylation step, any carbonylation process conditions can be used, provided that the carbonylation yields the desired acetyl halide product. The carbonylation agent, itself, can be any compound that is capable of transferring carbonyl (CO) to the methyl halide. Preferably, the carbonylation agent is carbon monoxide or an organometallic complex containing labile carbon monoxide, such as, transition metal salts and complexes, including Group VIII salts and complexes, such as the salts and complexes of palladium, iron, and cobalt, further including the carbonyl complexes of said transition metals. The molar ratio of carbonylation agent to methyl halide is typically at least 1:1, and preferably, greater than 1:1. More preferably, the molar ratio of carbonylation agent to methyl halide is greater than about 2:1. Preferably, the molar ratio of carbonylation agent to methyl halide is less than about 20:1, more preferably, less than about 10:1. Generally, the carbonylation step is conducted at a temperature greater than about 50° C., and at a temperature less than about 350° C. The pressure may range typically from atmospheric to higher pressures, generally from greater than about 7 psia (50 kPa) to less than about 725 psia (4,999 kPa). The total weight hourly space velocity (WHSV) of the carbonylation feed, including methyl halide and carbonylation agent, can vary widely from a value typically greater than about 0.1 g feed per g catalyst per hour (h$^{-1}$) to a value less than about 1,000 h$^{-1}$.

The product of the carbonylation process is acetyl halide, preferably, acetyl chloride. The subsequent hydrolysis of acetyl halide to acetic acid is simply effected by contacting acetyl halide with water under process conditions sufficient to form acetic acid. One skilled in the art will know the details of the hydrolysis of acetyl halide, as this step is a straight-forward hydrolysis of an acyl halide, which is well known and described, for example, in numerous organic chemistry textbooks.

The following examples are provided to further illustrate the process of this invention; but the examples should not be construed as limiting the invention in any manner. In light of the disclosure herein, those of skill in the art will recognize alternative embodiments of the invention that fall within the scope of the claims.

EXAMPLE 1

A catalyst composition comprising a porous lanthanum oxychloride was prepared as follows. Lanthanum chloride (LaCl$_3$7H$_2$O, 15 g) was dissolved in deionized water (100 ml) in a round-bottom flask. Ammonium hydroxide (6 M, 20 ml) was added to the lanthanum chloride solution with stirring. The mixture was centrifuged, and the excess liquid was decanted to yield a gel. In a separate container, calcium lactate (0.247 g, 0.0008 moles) was dissolved to form a saturated solution in deionized water. The calcium lactate solution was added with stirring to the lanthanum-containing gel. The gel was dried at 120° C. overnight. A dried solid was recovered, which was calcined under air in an open container at 550° C. for 4 hours to yield a porous lanthanum oxychloride catalyst (6.84 g). X-ray diffraction (XRD) of the solid indicated the presence of a quasi-crystalline form of lanthanum oxychloride.

The catalyst prepared hereinabove was crushed to 20×40 US mesh (0.85×0.43 mm) and evaluated in the oxidative chlorination of methane as follows. A tubular, nickel alloy reactor, having a ratio of length to diameter of 28.6/1 {6 inches (15.24 cm)×0.210 inches (0.533 cm)} was loaded with catalyst (2.02 g). The reactor was fed a mixture of methane, hydrogen chloride, and oxygen in the ratios shown in Table 1. The operating temperature was 400° C., and the operating pressure was atmospheric. The exit gases were analyzed by gas phase chromatography. Results are set forth in Table 1.

TABLE 1

Oxychlorination of Methane Over Lanthanum Catalyst to Methyl Chloride

| Mole Ratio $CH_4$:HCl:$O_2$ | WHSV $h^{-1}$ | Conv $CH_4$ (mol %) | Conv HCl (mol %) | Conv $O_2$ (mol %) | Sel $CH_3Cl$ (mol %) | Sel $CH_2Cl_2$ (mol %) | Sel CO (mol %) | Sel $CO_2$ (mol %) |
|---|---|---|---|---|---|---|---|---|
| 2:1:0.86 | 8.41 | 5.0 | 12.2 | 14.7 | 72.8 | 12.1 | 13.5 | 1.6 |
| 2:1:0.86 | 4.17 | 13.3 | 29.2 | 30.0 | 62.6 | 18.0 | 16.1 | 2.2 |
| 2:1:0.43 | 4.30 | 12.4 | — | 42.3 | 71.0 | 16.3 | 10.8 | 1.3 |
| 2:1:0.43 | 8.43 | 6.1 | — | 23.3 | 83.5 | 10.2 | 6.4 | 0.0 |

1. Process Conditions: 400° C., atmospheric pressure

EXAMPLE 2

This example illustrates an oxidative chlorination utilizing both methane and ethylene as hydrocarbon feeds. The catalyst was prepared by the following method. A solution of lanthanum chloride in water was prepared by dissolving one part of commercially available hydrated lanthanum chloride (Alfa Aesar) in 6.6 parts of deionized water. Rapid addition with stirring of 1.34 parts 6 M ammonium hydroxide in water caused the formation of a gel. The mixture was centrifuged, and the solution was decanted away from the gel and discarded. The collected gel was dried at 120° C. overnight and then calcined at 550° C. for 4 hours in air to yield an example of the catalyst. The XRD pattern matched that of LaOCl.

The catalyst was loaded into a nickel reactor with length/diameter ratio of 20/1. The reactor was brought to operating conditions of 452 degrees Celsius and near-ambient pressure. A feed containing methane/ethylene/hydrogen chloride/argon/oxygen in a molar ratio of 2.68:0.30:1.99:0.16:1.00 was contacted with the catalyst at a space-time of 7.6 seconds. Conversions of the reactants were as follows: ethylene, 46.4 percent; methane, 17.4 percent; hydrogen chloride, 36.4 percent; oxygen, 44.2 percent (calculated as mole percentages). Both methane and ethylene were consumed. Molar carbon selectivities were as follows: vinyl chloride, 24.7 percent; 1,2-dichloroethane, 6.1 percent; dichloroethylenes, 5.8 percent; methyl chloride 38.3 percent; methylene chloride, 12.5 percent; carbon monoxide, 11.3 percent; and carbon dioxide, 1.2 percent. With quantitative conversion of the chlorinated methanes to ethylene in a condensation reactor, these results allow calculation of an assumed product distribution for an envisioned methane to vinyl chloride process. Such a calculation yields molar selectivities on methane as follows: vinyl chloride monomer, 50.3 percent; 1,2-dichloroethane, 12.5 percent; 1,2-dichloroethylenes, 11.8 percent; carbon monoxide, 22.9 percent; and carbon dioxide, 2.5 percent.

What is claimed is:

1. A process of oxidative halogenation comprising contacting a reactant hydrocarbon selected from methane, a halogenated $C_1$ hydrocarbon, or a mixture thereof with a source of halogen and, optionally, a source of oxygen in the presence of a catalyst under process conditions sufficient to prepare a halogenated $C_1$ hydrocarbon having a greater number of halogen substituents as compared with the reactant hydrocarbon, the catalyst comprising a rare earth halide or rare earth oxyhalide substantially free of iron and copper, with the proviso that when cerium is present in the catalyst, then at least one other rare earth element is also present in the catalyst.

2. The process of claim 1 wherein the reactant hydrocarbon is selected from methane, chloromethane, bromomethane, iodomethane, dichloromethane, dibromomethane, diiodomethane, and chlorobromomethane.

3. The process of claim 1 wherein the reactant hydrocarbon is methane.

4. The process of claim 1 wherein the source of halogen is selected from the group consisting of elemental halogens, hydrogen halides, and halogenated hydrocarbons having one or more labile halogen substituents.

5. The process of claim 1 wherein the source of halogen is a source of chlorine or a source of bromine.

6. The process of claim 5 wherein the source of halogen is hydrogen chloride.

7. The process of claim 1 wherein the process is conducted at a molar ratio of reactant hydrocarbon to source of halogen of greater than about 1/1 to less than about 20/1.

8. The process of claim 1 wherein the process further comprises oxygen.

9. The process of claim 8 wherein the source of halogen is provided essentially in a stoichiometric or greater than stoichiometric amount with respect to the source of oxygen.

10. The process of claim 8 wherein the source of oxygen is selected from the group consisting of molecular oxygen and air.

11. The process of claim 8 wherein the process is conducted at a molar ratio of hydrocarbon to oxygen of greater than about 2/1 and less than about 20/1.

12. The process of claim 1 wherein the process further comprises a diluent.

13. The process of claim 12 wherein the diluent is selected from the group consisting of nitrogen, helium, argon, carbon monoxide, carbon dioxide, methane, and mixtures thereof.

14. The process of claim 13 wherein the diluent is used in an amount that is greater than about 10 mole percent and less than about 90 mole percent, based on the total moles of reactant hydrocarbon and diluent.

15. The process of claim 1 wherein the rare earth halide has a BET surface area greater than about 3 $m^2/g$.

16. The process of claim 15 wherein the rare earth halide has a BET surface area greater than about 15 $m^2/g$.

17. The process of claim 1 wherein the rare earth halide is represented by the formula $MX_3$, wherein M is at least one rare earth element selected from the group consisting of lanthanum, cerium, neodymium, praseodymium, dysprosium, samarium, yttrium, gadolinium, erbium, ytterbium, holmium, terbium, europium, thulium, lutetium, and mixtures thereof; and wherein X is chloride, bromide, or iodide.

18. The process of claim 17 wherein M is lanthanum or lanthanum in a mixture of other rare earth elements, and X is chloride.

19. The process of claim 1 wherein the rare earth oxyhalide support has a BET surface area greater than about 12 m²/g.

20. The process of claim 19 wherein the rare earth oxyhalide support has a BET surface area greater than about 20 m²/g.

21. The process of claim 1 wherein the rare earth oxyhalide support is represented by the formula MOX, wherein M is at least one rare earth selected from the group consisting of lanthanum, cerium, neodymium, praseodymium, dysprosium, samarium, yttrium, gadolinium, erbium, ytterbium, holmium, terbium, europium, thulium, lutetium, and mixtures thereof; and wherein X is chloride, bromide, or iodide.

22. The process of claim 21 wherein M is lanthanum or lanthanum in a mixture with other rare earth elements, and X is chloride.

23. The process of claim 1 wherein the catalyst is bonded to or extruded with a support.

24. The process of claim 1 wherein the process is conducted at a temperature greater than about 200° C. and less than about 600° C.

25. The process of claim 1 wherein the process is conducted at a pressure equal to or greater than about 14 psia (97 kPa) and less than about 150 psia (1,034 kPa).

26. The process of claim 1 wherein the process is conducted at a weight hourly space velocity of total feed, comprising the reactant hydrocarbon, the source of halogen, the optional source of oxygen, and an optional diluent, of greater than about 0.1 h$^{-1}$ and less than about 100 h$^{-1}$.

27. A process of oxidatively monohalogenating methane to form methyl chloride or methyl bromide, the process comprising contacting methane with hydrogen chloride or hydrogen bromide, and oxygen in the presence of a catalyst at a temperature greater than about 300° C. and less than about 500° C. such that methyl chloride or methyl bromide is formed, the catalyst comprising a rare earth halide or rare earth oxyhalide compound that is essentially free of iron and copper, with the proviso that when cerium is present in the catalyst, then at least one rare earth element is also present in the catalyst.

28. The process of claim 27 wherein the catalyst is a rare earth chloride or rare earth oxychloride.

29. The process of claim 28 wherein the rare earth is lanthanum or lanthanum in a mixture with other rare earth elements.

30. The process of claim 27 wherein the selectivity to methyl chloride or methyl bromide is greater than about 60 mole percent.

31. A process of preparing methyl alcohol comprising (a) contacting methane with a source of halogen, and optionally, a source of oxygen in the presence of a catalyst under oxidative monohalogenation process conditions sufficient to prepare methyl halide, the catalyst comprising a rare earth halide or rare earth oxyhalide essentially free of iron and copper, with the proviso that when the catalyst contains cerium, the catalyst also contains at least one other rare earth element; and thereafter (b) contacting the methyl halide thus prepared with water in the presence of a hydrolysis catalyst under conditions sufficient to prepare methyl alcohol and co-product hydrogen halide; and optionally (c) recycling the co-product hydrogen halide to the oxidative halogenation process step (a).

32. The process of claim 31 wherein the source of halogen is hydrogen chloride, and oxygen is employed in process step (a).

33. The process of claim 31 wherein the rare earth halide or rare earth oxyhalide is a rare earth chloride or a rare earth oxychloride.

34. The process of claim 33 wherein the rare earth is lanthanum or lanthanum in a mixture with other rare earth elements.

35. The process of claim 31 wherein the hydrolysis catalyst is selected from the group consisting of alumina, zeolites of the ZSM structure code, alkali and alkaline earth metal hydroxides and alkoxides, alkyl ammonium hydroxides, amines, halide complexes of platinum, palladium, and nickel, and metal oxides and hydroxides of Group IIA and the transition elements supported on γ-alumina or activated carbon.

36. The process of claim 31 wherein in step (b) the molar ratio of water to methyl halide is greater than about 1:1 and less than about 20:1.

37. The process of claim 31 wherein in step (b), the hydrolysis is conducted at a temperature greater than about 85° C. and less than about 600° C., and at a pressure greater than about 7 psia (50 kPa) and less than about 725 psia (4,999 kPa).

38. The process of claim 31 wherein the co-product hydrogen halide is recycled to the oxidative halogenation process of step (a).

39. A process of condensing methyl halide to form light olefins and/or gasolines comprising (a) contacting methane with a source of halogen, and optionally, a source of oxygen in the presence of a catalyst under oxidative halogenation process conditions sufficient to prepare methyl halide and, optionally, dihalomethane, the catalyst comprising a rare earth halide or rare earth oxyhalide being essentially free of iron and copper, with the proviso that when the catalyst contains cerium, the catalyst also contains at least one other rare earth element; and thereafter (b) contacting the methyl halide and, optionally, dihalomethane thus prepared with a condensation catalyst under conditions sufficient to prepare at least one light olefin, at least one $C_{5+}$ gasoline, or a combination thereof; and (c) optionally recycling the co-product hydrogen halide to the oxidative halogenation step (a).

40. The process of claim 39 wherein the source of halogen is hydrogen chloride, and oxygen is employed in process step (a).

41. The process of claim 40 wherein oxygen is provided as essentially pure oxygen or as air.

42. The process of claim 39 wherein the rare earth halide or rare earth oxyhalide is a rare earth chloride or rare earth oxychloride.

43. The process of claim 42 wherein the rare earth is lanthanum or lanthanum in a mixture with other rare earth elements.

44. The process of claim 39 wherein the condensation catalyst is selected from the group consisting of aluminosilicates of the DCM-2 and ZSM structure codes, aluminophosphates, borosilicates, silicates, and silicoaluminophosphates.

45. The process of claim 39 wherein the process temperature is greater than about 250° C. and less than about 600° C., and wherein the process pressure is greater than about 0.1 psi absolute (689 Pa) and less than about 300 psi absolute (2,068 kPa).

46. The process of claim 39 wherein the co-product hydrogen halide from step (b) is recycled to the oxidative halogenation process of step (a).

47. A process of preparing vinyl halide monomer comprising (a) contacting methane with a first source of halogen, and optionally, a first source of oxygen in the presence of a first oxidative halogenation catalyst under process conditions sufficient to prepare methyl halide and, optionally, dihalomethane, the catalyst comprising a rare earth halide or rare earth oxyhalide being essentially free of iron and copper, with the proviso that when the catalyst contains cerium, the catalyst also contains at least one other rare earth element; (b) contacting the methyl halide and, optionally, dihalomethane thus prepared with a condensation catalyst under condensation conditions sufficient to prepare ethylene and co-product hydrogen halide; (c) contacting ethylene with a second source of halogen, and optionally, a second source of oxygen in the presence of a second oxidative halogenation catalyst under oxidative halogenation process conditions, and optional thermal cracking conditions, sufficient to prepare vinyl halide monomer; and optionally (d) recycling the co-product hydrogen halide to process steps (a) and/or (c).

48. The process of claim 47 wherein the first and second sources of halogen are both hydrogen chloride, and oxygen is employed in process steps (a) and (c).

49. The process of claim 47 wherein the first and second sources of oxygen are provided as essentially pure oxygen, or air, or oxygen-enriched air.

50. The process of claim 47 wherein in step (a) the rare earth halide or rare earth oxyhalide is a rare earth chloride or rare earth oxychloride.

51. The process of claim 50 wherein the rare earth is lanthanum or lanthanum in a mixture with other rare earth elements.

52. The process of claim 47 wherein the condensation catalyst is selected from the group consisting of aluminosilicates of the DCM-2 and ZSM structure codes, aluminophosphates, borosilicates, silicates, and silicoaluminophosphates.

53. The process of claim 47 wherein the condensation process temperature is greater than 250° C. and less than about 600° C., and wherein the condensation process pressure is greater than about 0.1 psi absolute (689 Pa) and less than about 300 psi absolute (2,068 kPa).

54. The process of claim 47 wherein in step (c) the second oxidative halogenation catalyst comprises a rare earth halide or rare earth oxyhalide being essentially free of iron and copper, with the proviso that when the catalyst contains cerium, the catalyst also contains at least one other rare earth element.

55. The process of claim 47 wherein ethylene from step (b) and lo methane are co-fed to the oxidative halogenation reactor of step (a) to produce a mixture of methyl halide and vinyl halide, thereby combining steps (a) and (c) in one reactor.

56. The process of claim 56 wherein the mixture of methyl halide and vinyl halide are separated; vinyl halide is collected as a product; and the methyl halide is recycled to step (b) to produce ethylene.

57. A process of preparing acetic acid comprising (a) contacting methane with a source of halogen and, optionally, a source of oxygen in the presence of a an oxidative halogenation catalyst under oxidative halogenation process conditions sufficient to prepare methyl halide, (b) contacting the methyl halide thus produced with a source of carbonyl in the presence of a carbonylation catalyst under carbonylation process conditions sufficient to prepared acetyl halide; and thereafter (c) hydrolyzing the acetyl halide thus produced to yield acetic acid.

58. The process of claim 58 wherein the oxidative halogenation catalyst is a rare earth halide or rare earth oxyhalide, being essentially free of copper and iron, and with the proviso that when cerium is present in the catalyst, at least one other rare earth element is also present in the catalyst.

* * * * *